(12) United States Patent
Fujikawa et al.

(10) Patent No.: US 8,110,178 B2
(45) Date of Patent: Feb. 7, 2012

(54) DENTAL-PLAQUE DETECTION SYSTEM AND DENTAL-PLAQUE DETECTION METHOD

(75) Inventors: Haruhiko Fujikawa, Hiratsuka (JP); Kouichi Saitoh, Kamakura (JP)

(73) Assignee: Lion Corporation, Sumida-ku, Tokyo (JP)

( * ) Notice: Subject to any disclaimer, the term of this patent is extended or adjusted under 35 U.S.C. 154(b) by 1150 days.

(21) Appl. No.: 11/662,346

(22) PCT Filed: Sep. 6, 2005

(86) PCT No.: PCT/JP2005/016342
§ 371 (c)(1),
(2), (4) Date: Jul. 11, 2007

(87) PCT Pub. No.: WO2006/028099
PCT Pub. Date: Mar. 16, 2006

(65) Prior Publication Data
US 2007/0280888 A1 Dec. 6, 2007

(30) Foreign Application Priority Data
Sep. 10, 2004 (JP) ................ P2004-263879

(51) Int. Cl.
| | |
|---|---|
| A61C 19/04 | (2006.01) |
| A61C 3/00 | (2006.01) |
| C09D 11/00 | (2006.01) |
| A61B 1/00 | (2006.01) |
| A61B 1/24 | (2006.01) |
| A61K 8/00 | (2006.01) |
| C08K 5/00 | (2006.01) |

(52) U.S. Cl. .......... 424/9.71; 424/49; 424/58; 426/250; 433/25; 433/29; 106/493; 604/19; 604/20

(58) Field of Classification Search ................ 424/9.71, 424/49; 433/29
See application file for complete search history.

(56) References Cited

U.S. PATENT DOCUMENTS

| | | |
|---|---|---|
| 3,309,274 A | 3/1967 | Brilliant |
| 3,711,700 A | 1/1973 | Westlund, Jr. et al. |
| 4,266,535 A | 5/1981 | Moret |
| 4,292,664 A | 9/1981 | Mack |
| 5,957,687 A | 9/1999 | Brilliant |
| 6,186,780 B1 * | 2/2001 | Hibst et al. ............. 433/29 |
| 6,485,300 B1 | 11/2002 | Muller et al. |
| 2003/0143510 A1 | 7/2003 | Berube-Lauziere et al. |
| 2003/0173525 A1 * | 9/2003 | Seville ............. 250/458.1 |

FOREIGN PATENT DOCUMENTS

| | | |
|---|---|---|
| JP | 64-86965 | 3/1989 |
| JP | 4-5222 | 1/1992 |
| JP | 04-182410 | 6/1992 |
| JP | 6-73531 | 9/1994 |
| JP | 10-120539 | 5/1998 |
| JP | 3066528 | 12/1999 |
| JP | 2001-322923 | 11/2001 |
| JP | 2002-20278 | 1/2002 |
| JP | 2002-85351 | 3/2002 |
| JP | 2002-515276 | 5/2002 |
| JP | 3314978 | 6/2002 |
| JP | 2002-226314 | 8/2002 |
| JP | 2004151002 | 10/2002 |
| JP | 2003-40722 | 2/2003 |
| JP | 2003-81731 | 3/2003 |
| JP | 2003-520635 | 7/2003 |
| JP | 2004-65994 | 3/2004 |
| JP | 2004154211 | 6/2004 |
| WO | WO 92/06671 | 4/1992 |

OTHER PUBLICATIONS

De Josselin de Jong, et al. "A new method for in vivo quantification of changes in initial enamel caries with laser fluorescence." *Caries Research*, S.Karger AG, Basel, CH, vol. 29, Jan. 1, 1995, pp. 2-7.

* cited by examiner

*Primary Examiner* — Frederick Krass
*Assistant Examiner* — Lezah Roberts
(74) *Attorney, Agent, or Firm* — Merchant & Gould P.C.

(57) ABSTRACT

A dental-plaque detection system and dental-plaque detection method which are excellent in the detection accuracy of dental plaques and also capable of improving the situation to stain sites other than dental plaques (such as interdental parts and gums) are provided. The dental-plaque detection system includes a dental-plaque staining agent, which contains at least one selected from yellow pigment of beni-koji, turmeric extracts, and curcumin; and a light-emitting apparatus, which outputs light having a wavelength within a range of 250 to 500 nm to an object in the oral cavity where the dental-plaque staining agent is attached. The dental-plaque detection method includes attaching a dental-plaque staining agent, which contains at least one selected from yellow pigment of beni-koji, turmeric extracts, and curcumin onto an object in the oral cavity; and thereafter irradiating light having a wavelength within a range of 250 to 500 nm onto the object.

5 Claims, 4 Drawing Sheets

US 8,110,178 B2

DENTAL-PLAQUE DETECTION SYSTEM AND DENTAL-PLAQUE DETECTION METHOD

TECHNICAL FIELD

The present invention relates to a dental-plaque detection system and a dental-plaque detection method.

Priority is claimed on Japanese Patent Application No. 2004-263879, filed Sep. 10, 2004, the content of which is incorporated herein by reference.

BACKGROUND ART

Caries or periodontal diseases are thought to be infectious diseases caused by bacteria present in dental plaques and it is known that the removal of dental plaques is highly important for the health of oral cavities. However, dental plaques are not easy to identify by the naked eye and it is difficult to confirm their attachment site and extent thereof precisely.

Accordingly, dental plaques are generally stained with dental-plaque staining agents, which contain dyes, to reveal their locations in order to uncover the attached dental plaques. Among the dental-plaque staining agents which have conventionally been commercially available, although tar dyes such as Red No. 3 (erythrosine), Red No. 104 (phloxine), and Red No. 105 (rose bengal) have been often used as dye components, these dental-plaque staining agents stain not only dental plaques red but also gums, oral mucosa, lips, or the like indiscriminately. Since the red stains are not easy to remove, cannot be removed sufficiently by normal toothbrushing using a toothbrush, and remain on interdental parts, gums, lips, or the like, there was a problem of causing an uncomfortable feeling.

A yellow pigment of beni-koji and turmeric are known as staining agents used for other purposes.

The abovementioned yellow pigment of beni-koji is a yellow pigment obtained from the culture medium of beni-koji mold, which belongs to Ascomycota, and is used in fish paste, fish eggs, jellies, frozen desserts, or the like for coloring purposes. As for intraoral use, a composition for the oral cavity, which contains cationic antiseptics that prevent water-soluble dyes to bleach, is disclosed (Patent document 1).

The aforementioned turmeric is a perennial plant, which belongs to Zingiberaceae, and the rhizome extract containing curcumin has been used not only as a pigment, which is simply added to food products or the like, but also as a herbal medicine such as a cholagogue or an aromatic stomachic for many years. In addition, it is attracting attention in recent years since it is said to be effective in suppressing skin-, gastric-, and colon cancers, preventing complications of liver damage and diabetes, and improving antiallergic action. On the other hand, as for use in the oral cavity, prevention of oral-cavity cancer by healing the precancerous lesion of the oral cavity (Patent document 2), antimicrobial activity against bacteria which cause periodontal diseases (Patent document 3), prevention of gingivitis and periodontitis (Patent document 4), an antioxidant (Patent document 5), or the like have been disclosed. However, these are not intended to stain dental plaques.

In addition, techniques to detect dental plaques by staining them with dyes or fluorescent agents such as Red No. 3 (erythrosine), Red No. 213 (rhodamine B), Yellow No. 201 (fluorescein), and chlorophyll and then irradiating specific light onto them have been disclosed (Patent document 6, Patent document 7, Patent document 8, Patent document 9, Patent document 10). Methods such as these using dyes and light concomitantly require dyes to not only be excited by the light and fluoresce but also to attach themselves firmly to dental plaques. However, since currently known fluorescent agents such as chlorophyll or fluorescein do not stain dental plaques sufficiently, there was a problem in reliability of detection results of dental plaques.

With such a background, demands for a method to detect dental plaques with high precision have been increasing.

Furthermore, instruments to irradiate light in oral cavities (Patent document 11, Patent document 12) and a method to irradiate specific light to detect caries (Patent document 13) have been disclosed. Additionally, techniques to detect dental plaques solely due to light by irradiating specific light (Patent document 14, Patent document 15) have been disclosed.

However, from initial dental plaques which attach to the tooth surface to dental plaques which turned into dental calculi, dental plaques are known to change their structures and inhabiting bacterial species with time and thus, the above techniques to detect dental plaques solely by specific light have not been possible to detect dental plaques which are in the initial phase of their formation.

[Patent document 1] Japanese Unexamined Patent Application, First Publication No. Hei 10-120539
[Patent document 2] Japanese Laid-Open Patent Application No. 2002-20278
[Patent document 3] Japanese Unexamined Patent Application, First Publication No. Hei 4-5222
[Patent document 4] Japanese Patent Publication No. 3314978
[Patent document 5] Japanese Laid-Open Patent Application No. 2001-322923
[Patent document 6] U.S. Pat. No. 3,309,274
[Patent document 7] U.S. Pat. No. 3,711,700
[Patent document 8] U.S. Pat. No. 4,292,664
[Patent document 9] U.S. Pat. No. 4,266,535
[Patent document 10] U.S. Pat. No. 5,957,687
[Patent document 11] Japanese Laid-Open Patent Application No. 2002-85351
[Patent document 12] Japanese Utility Model Registration No. 3066528
[Patent document 13] Japanese Patent Publication No. 1944198
[Patent document 14] Published Japanese translation No. 2002-515276 of PCT International Publication
[Patent document 15] Japanese Laid-Open Patent Application No. 2004-65994

DISCLOSURE OF THE INVENTION

Problems to be Solved by the Invention

The present invention is made in view of the aforementioned circumstances and its object is to provide a dental-plaque detection system and dental-plaque detection method which are excellent in the detection accuracy of dental plaques and also capable of improving the situation to stain sites other than dental plaques (such as interdental parts and gums).

Means for Solving the Problem

As a result of intensive research in order to achieve the aforementioned object, the present inventors discovered the following. By irradiating light which has a wavelength within 250 to 500 nm after applying a dental-plaque staining agent, which contains at least one selected from the yellow pigment of beni-koji, turmeric extracts, and curcumin, in oral cavities, dental plaques can be detected more effectively than using commercially available dental-plaque staining agents and in particular, dental plaques which are in the initial phase of their formation can also be detected with high precision and furthermore, discomfort (indiscriminate staining of gums and interdental parts) brought about by red dental-plaque staining agents, which have conventionally been commercially available, can be alleviated.

Moreover, the present inventors discovered that compared to conventional techniques using fluorescent agents such as fluorescein, the method of the present invention considerably improves visibility of dental plaques including dental plaques which are in the initial phase of their formation although the sites of dental plaques are not visible under natural light and discomfort due to the staining does not occur.

In other words, the present invention provides a dental-plaque detection system including a dental-plaque staining agent, which contains at least one selected from the yellow pigment of beni-koji, turmeric extracts, and curcumin, and a light-emitting apparatus which outputs light having a wavelength within a range of 250 to 500 nm onto an object in the oral cavity where the dental-plaque staining agent is attached.

It is preferable that the light-emitting apparatus be provided with a light-emitting device which outputs light having a wavelength within a range of 250 to 500 nm. Alternatively, it is preferable that the light-emitting apparatus be provided with either a light-emitting device or a lamp, together with a filter, which selectively transmits light having a wavelength within a range of 250 to 500 nm.

Moreover, the configuration below is preferable. The light-emitting apparatus is equipped with a light-receiving section and an image-displaying apparatus and a probe are individually connected to the light-emitting apparatus and it is configured so that the probe can irradiate light outputted from the light-emitting apparatus towards the aforementioned object and also image information of the object, which is irradiated with light, can be sent to the light-receiving section and the image-displaying apparatus can display image information of the object received by the light-receiving section.

It is preferable that a high pass filter which transmits light having a wavelength of 520 nm or more among the reflection of the light, which is irradiated onto the object, be provided in the object side of the probe.

In addition, the present invention provides an illuminator for dental-plaque detection, which is an illuminator equipped with a light source which irradiates light onto an object in the oral cavity where a dental-plaque staining agent, which contains at least one selected from the yellow pigment of beni-koji, turmeric extracts, and curcumin, is attached, and in which the light source has a light-emitting device which outputs light with a wavelength within a range of 250 to 500 nm.

Moreover, the present invention provides a toothbrush attached with a light source for dental-plaque detection, which is equipped with a light source which irradiates light onto an object in the oral cavity where a dental-plaque staining agent, which contains at least one selected from the yellow pigment of beni-koji, turmeric extracts, and curcumin, is attached, and in which the light source has a light-emitting device which outputs light with a wavelength within a range of 250 to 500 nm.

The dental-plaque staining agent for the dental-plaque detection system of the present invention contains at least one selected from the yellow pigment of beni-koji, turmeric extracts, and curcumin.

The content of the yellow pigment of beni-koji in the dental-plaque staining agent for the dental-plaque detection system is preferably 0.01 to 5 mass %.

Additionally, the content of turmeric extracts or curcumin in the dental-plaque staining agent for the dental-plaque detection system is preferably 0.01 to 3 mass %.

The dental-plaque detection method of the present invention is a method which includes attaching of the dental-plaque staining agent, which contains at least one selected from the yellow pigment of beni-koji, turmeric extracts, and curcumin, to an object in the oral cavity and thereafter irradiating light having a wavelength within a range of 250 to 500 nm onto the object.

Effects of the Invention

According to the dental-plaque detection method of the present invention, detection accuracy of dental plaques will be excellent and moreover, the situation where sites other than dental plaques (such as interdental parts and gums) are stained can be improved.

The dental-plaque detection system, the illuminator for dental-plaque detection, the toothbrush attached with a light source for dental-plaque detection, and the dental-plaque staining agent for the dental-plaque detection system of the present invention can favorably be used in conducting the dental-plaque detection method of the present invention and they are excellent in terms of the detection accuracy of dental plaques and moreover, they can improve the situation where sites other than dental plaques (such as interdental parts and gums) are stained.

BRIEF DESCRIPTION OF THE REFERENCE SYMBOLS

Figure 1:
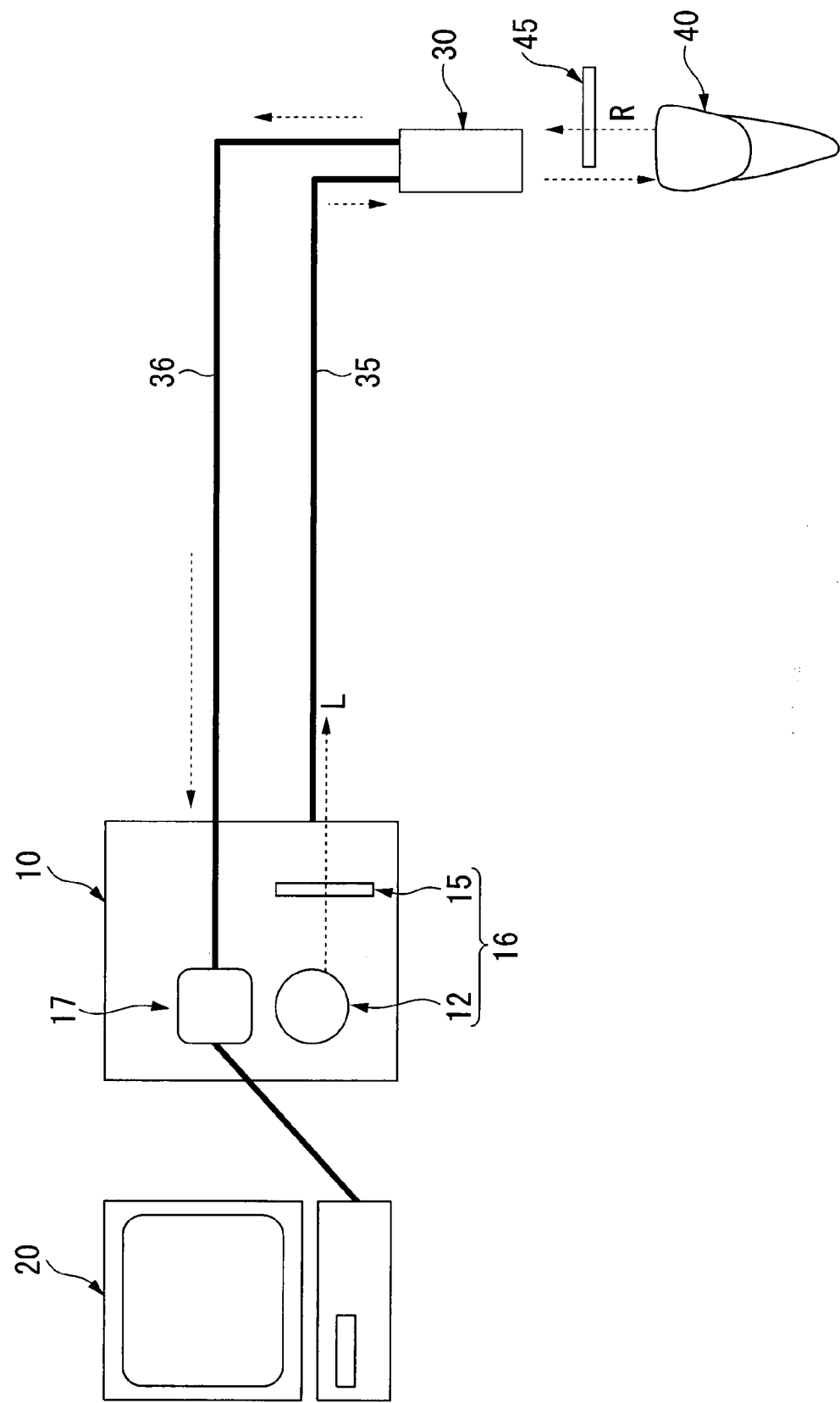
FIG. 1 is a schematic configuration diagram showing one example of an embodiment of the dental-plaque detection system of the present invention.

10 . . . light-emitting apparatus, 12 . . . light source, 15 . . . band-pass filter, 16 . . . light-emitting section, 17 . . . light-receiving section, 20 . . . image-displaying apparatus, 30 . . . probe, 35 . . . first cable, 36 . . . second cable, 40 . . . object in oral cavity, 45 . . . high-pass filter, 50/70 . . . grip section, 52/72 . . . light source, 53/73 . . . battery box, 54/74 . . . switch, 55 . . . head section, 56 . . . light-emitting orifice, 58 . . . hand grip section, 59 . . . optical waveguide, 60/80/80' . . . wiring, 75 . . . mirror section, 77 . . . cap section, 77a . . . back end section, 78/78' . . . stick section, 78a . . . diameter expanding section, 79 . . . mirror stick section, L . . . light, R . . . reflection

BEST MODES FOR CARRYING OUT THE INVENTION

Although embodiments of the present invention will be described next in detail using figures, the present invention is not limited to the embodiments described below. In addition, in order to express the scale of each constituting part in the figures with ease, each constituting part is described while changing the scale thereof.

A dental-plaque detection system, illuminator for dental-plaque detection, toothbrush attached with a light source for dental-plaque detection, dental-plaque staining agent, and dental-plaque detection method of the present invention can be used for examining the presence/absence of dental plaques and sites and extent of their attachment.

It is known that dental plaques generally go through an initial state where bacteria in the oral cavity attach to a protein coat on the tooth surface and after the bacterial formation of external polysaccharides, the structure and bacterial species of dental plaques change with time since various types of indigenous bacteria further attach/colonize thereon to multiply. Accordingly, the dental plaques according to the present invention refer to a generic term of complexes, which are not limited to the passage of time, which attach/fix onto the surface of teeth, and which are composed from bacteria and/or their products including those that are dental-calculi like. In other words, the dental plaques according to the present invention refer to a generic term including initial dental plaques and dental calculi.

The dental-plaque detection method of the present invention attaches a dental-plaque staining agent, which contains at least one selected from the yellow pigment of beni-koji, turmeric extracts, and curcumin, onto an object in the oral cavity and thereafter, makes only the dental plaques, which are attached to the object, visible as if they are stained with a fluorescent color by exciting the dental-plaque staining agent due to the irradiation of light having a wavelength within a range of 250 to 500 nm onto the object. Specifically, the object in the oral cavity refers to the surface of teeth.

The yellow pigment of beni-koji used in the present invention is obtained by methods such as drying and grinding of the culture media of beni-koji molds of Ascomycota, for example, *Monascus anka*, *Monascus purpureus*, or the like, followed by the extraction of the resultant material with hydrochloric acid-acidic ethanol and neautralizaton thereof and it is a yellow pigment having xanthomonasins as a major component.

The formulae (1) and (2) below are the chemical structures of the aforementioned yellow pigment of beni-koji.

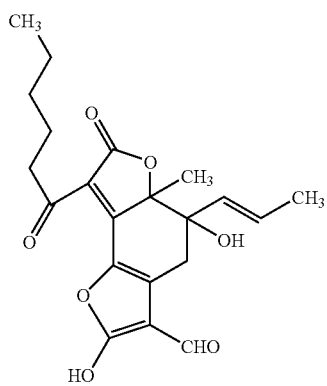
(1)

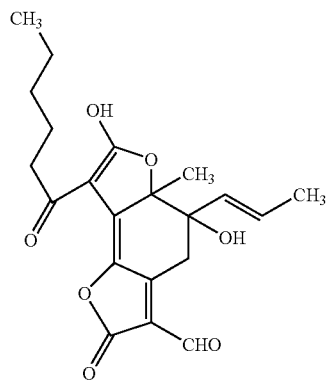
(2)

The turmeric extracts used in the present invention originate from rhizomes of turmeric, which is a plant belonging to Zingiberaceae, and although they contain curcumin and curcumin analogues which are represented by the general formula (3) below, the major component thereof is curcumin and the simple substance of curcumin or curcumin, which is processed to be aqueous, can also be used.

Moreover, although there are several types of turmerics; for example, "spring turmeric" (*Curcuma aromatica* Salisb.), "autumn turmeric" (*Curcuma longa* L.), or fermented turmeric, which is fermented with lactic acid bacteria in order to remove bitter tastes, any of them can be used as long as they contain curcumin or curcumin analogues. The turmeric extracts or curcumin are generally extracted from turmeric rhizomes and for example, a method using organic solvents such as ethanol or propylene glycol, or fats and oils is used for the extraction.

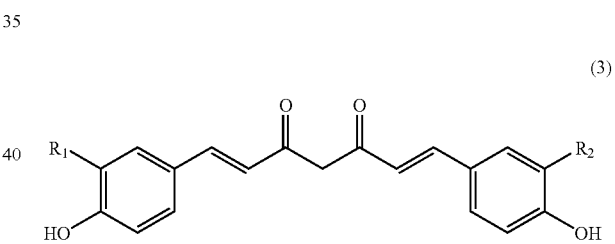
(3)

In the case of curcumin, $R_1$ represents $OCH_3$ and $R_2$ represents $OCH_3$ in the general formula (3).

In the case of curcumin analogue A, $R_1$ represents H and $R_2$ represents $OCH_3$ in the general formula (3).

In the case of curcumin analogue B, $R_1$ represents H and $R_2$ represents H in the general formula (3).

Commercially available products may be used as active ingredients of the abovementioned dental-plaque staining agents such as the yellow pigment of beni-koji.

That is, the yellow pigment of beni-koji which can be used in the present invention includes "SunYellow No. 1244" (product name) manufactured by San-Ei Gen F.F.I. Co., Ltd., "TS yellow M" and "TS yellow MP" (product names) manufactured by Taisho Technos Co., Ltd.; "Pharcolex turmeric B" and "Pharcolex turmeric E" (product names) manufactured by Ichimaru Pharcos Co., Ltd.; and "Monascus Yellow-S" (product name) manufactured by Kiriya Chemical Co., Ltd.

The turmeric extracts which can be used in the present invention include curcumin AL (product name) manufactured by San-Ei Gen F.F.I. Co., Ltd.; "turmeric extract J", "turmeric extract BG", and "concentrated turmeric extract powder M" (product names) manufactured by Maruzen Pharmaceuticals Co., Ltd.; "TS Yellow No. 3 GH", "TS Yellow No. 3P", and "TS Yellow No. 3PC" (product names) manufactured by Taisho Technos Co., Ltd.; "Pharcolex turmeric B" and "Pharcolex turmeric E" (product names) manufactured by Ichimaru Pharcos Co., Ltd. and "Wiener Yellow Conc" (product name) manufactured by Kiriya Chemical Co., Ltd.

Although the aforementioned yellow pigment of beni-koji is generally sold in the form of powder or liquid, since it is a mixture of xanthomonasins represented by the formulae (1) and (2), it is often the case that the pigment content in the yellow pigment of beni-koji of commercial items cannot be measured precisely. Accordingly, color valence is defined as an alternative standard to concentration. Although the method of measuring color valence is as described in Japanese Standards of Food Additives, the method below is used in the case of yellow pigment of beni-koji.

Pigment sample is diluted with 50 volume % ethanol so that the absorbance thereof at 460 nm is within a range of 0.3 to 0.7 to prepare a test liquid. The absorbance A at 460 nm of a liquid layer having a length of 1 cm is measured by using 50 volume % ethanol as a control and the color valence is determined by the equation below.

$$\text{Color valence} = 10 \times A \times F / \text{amount of samples}$$

(in the formula, F represents dilution rate for preparing samples so that the measured absorbance thereof will be within the range of 0.3 to 0.7)

The color valence of the yellow pigment of beni-koji of commercial items used for the dental-plaque staining agents of the present invention is preferably 20 to 200 and more preferably 50 to 150.

The loadings of the yellow pigment of beni-koji in the dental-plaque staining agents of the present invention are 1 to 100 mass % when using the yellow pigment of beni-koji of commercial items with a color valence of 60, for example, and are 0.5 to 100 mass % when using the yellow pigment of beni-koji of commercial items with a color valence of 120.

The content of the yellow pigment of beni-koji in the dental-plaque staining agents of the present invention is preferably 0.01 to 5 mass % on a net basis of major pigments containing xanthomonasins represented by the formulae (1) and (2). Considering more effective improvement of stainability of dental plaques and that the upper limit of the concentration of the yellow pigment of beni-koji of commercial items is approximately 1% for liquid forms and approximately 2% for powder forms, the content of the yellow pigment of beni-koji in the dental-plaque staining agents of the present invention is more preferably 0.1 to 1 mass %.

The content of turmeric extracts or curcumin in the dental-plaque staining agents of the present invention is preferably 0.01 to 3 mass % as a turmeric pigment or curcumin and 0.1 to 2 mass % is more preferable for the improvement of stainability of dental plaques and reduction of adhesive properties thereof to gums or interdental parts.

In the method to detect dental plaques by attaching the dental-plaque staining agent of the present invention which contains at least one selected from the yellow pigment of beni-koji, turmeric extracts, and curcumin, and thereafter, irradiating light (the light having a wavelength within a range of 250 to 500 nm), which excites the dental-plaque staining agent, it is more preferable to use the yellow pigment of beni-koji than turmeric extracts or curcumin for visibility of dental plaques, prevention of staining other sites such as gums and interdental parts, and removability by cleaning practice such as tooth brushing.

The dental-plaque staining agent of the present invention can be used by preparing thereof in forms such as liquid, fluid, gels, pastes, and tablets. In this case, for example, when using the dental-plaque staining agent in the form of a solution, methods such as the swab coating method, brush coating method, direct drop method, and mouth wash method may be adopted. Additionally, when using the dental-plaque staining agent in the form of a tablet, tablets are chewed while being mixed well with saliva produced to reach all over the tooth surface for use, or, may also be used as a solution by dissolving in water or the like at the time of use.

The dental-plaque staining agent of the present invention, depending on the form thereof, can be mixed with arbitrary components in addition to the aforementioned components within the range where stainability is not affected by adverse effects where appropriate. For example, binders, thickening agents, surfactants, sweeteners, antiseptics, perfumes, staining accelerators, pH adjusting agents, solvents such as water, or other components can be mixed.

Although concrete examples of arbitrary components are shown below, the components which can be mixed with the dental-plaque staining agent of the present invention are not limited to them.

Binders can appropriately be selected, for example, from the following: carageenan, sodium alginate, xanthan gum, pullulan, gelatin, carboxymethylcellulose, sodium carboxymethylcellulose, methylcellulose, hydroxyethylcellulose, gum Arabic, guar gum, locust bean gum, sodium polyacrylate, polyvinyl alcohol, polyvinylpyrrolidone, montmorillonite, kaolin, hydrated silica, aluminum silicate, magnesium silicate, and hectorite.

Thickening agents can appropriately be selected, for example, from the following: propylene glycol, butylene glycol, sorbitol, glycerin, polyethylene glycol, and xylitol.

As surfactants, for example, the following can appropriately be selected: anionic activators such as lauryl sulfate, α-olefin sulfonate, N-acylsarcosine, and aliphatic monoglyceride sulfate; nonionic activators such as sucrose aliphatic acid ester, polyoxyethylene-polyoxypropylene glycol block polymer, polyoxyethylene hardened castor oil, and fatty acid monoalkanolamide; and amphoteric activators such as imidazolinium betaine, alkylamide betaine, and amine oxide.

Sweeteners can appropriately be selected, for example, from the following: saccharin sodium, stevioside, neo-hesperidyl dihydrochalcone, glycyrrhizin, perillartin, p-methoxycinnamic aldehyde, and thaumatin.

Antiseptics can appropriately be selected, for example, from the following: sodium benzoate, paraoxybenzoate ester, methylparaben, ethylparaben, butylparaben, and ethylenediaminetetraacetate.

Perfumes can appropriately be selected, for example, from the following perfume materials: essential oil such as peppermint/spearmint, essence of fruits such as lemon/strawberry, 1-menthol, carvone, eugenol, anethole, linalool, limonene, ocimene, cineole, n-decyl alcohol, citronellol, vanillin, α-terbineol, methyl salicylate, thymol, rosemary oil, sage oil, perilla oil, lemon oil, and orange oil.

As staining accelerators, for example, the following can be selected where necessary; calcium carbonate, calcium hydrogen phosphate dihydrate and calcium hydrogen phosphate anhydride, calcium pyrophosphate, sodium phosphate, insoluble sodium metaphosphate, tribasic magnesium phosphate, magnesium carbonate, amorphous silica, crystalline silica, sedimentary amorphous silica, zeolite, aluminosilicate, aluminum oxide, aluminum hydroxide, resin, polysaccharides such as starch and dextran and decomposition products thereof such as dextrin, and reduced starch decomposition products.

The dental-plaque staining agent of the present invention may adjust pH thereof within a safe range in the oral cavity while not imposing adverse effects on the stainability of pigments (active ingredients of dental-plaque staining agents) used. The pH adjusting agent which can be used can appropriately be selected, for example, from the following: hydrochloric acid, phosphoric acid, citric acid, malic acid, acetic acid, and salts thereof; sodium hydroxide, potassium hydroxide, sodium silicate, magnesium silicate, sodium bicarbonate, calcium oxide, magnesium oxide, and tetrasodium pyrophosphate.

Furthermore, it is possible to use the following as other components within a pharmaceutically allowable range: fluorides such as sodium fluoride, sodium monofluorophosphate, and stannous fluoride; bactericides/antibacterial agents such as chlorhexidine, triclosan and cetylpyridinium chloride; dental-calculi preventing agents such as condensed phosphate and ethanehydroxydiphosphonate; anti-inflammatory agents such as tranexamic acid and dipotassium glycyrrhizin; enzymatic agents such as dextranase and mutanase; astringents such as sodium chloride and aluminum lactate; suppressants of hyperesthesia such as potassium nitrate and strontium chloride; dental-plaque inhibitors such as zinc citrate and gluconic acid. Moreover, the following pigments of 0.001 to 0.5 mass % can be mixed therein within a range where visibility of the present invention is not inhibited: Red No. 104 (phloxine), Red No. 105 (rose bengal), Red No. 106 (acid red), Yellow No. 5 (sunset yellow), carthamus (safflower) yellow, paprika (capsicum) pigment, red pigment from benikoji, marigold pigment, spirulina blue pigment, riboflavin (vitamin B2), saffron extracts, methyl N-methylanthranilate, cumin extracts, and vitamin A. Furthermore, ethanol, water, or the like can be mixed as a solvent. In the case of tablets, known components for tablets such as bonding agents and disintegrators can be used.

Note that the loadings of these arbitrary components can be the usual dose within the range where the effects of the present invention are not impaired.

For light irradiated onto an object in the oral cavity which is attached with the dental-plaque staining agent of the present invention, one having a wavelength within a range of 250 to 500 nm is used. As long as light having a wavelength of the aforementioned range can be irradiated, any type of light source may be used. For example, light-emitting devices such as the light-emitting diode (LED) irradiating light having a wavelength within the range of 250 to 500 nm can be used.

In addition, it is also possible to use a xenon lamp, xenon flash lamp, metal halide lamp, hollow cathode lamp, or the like. When the light outputted from the lamp has a wavelength of a wide range, by using a band-pass filter, which selectively transmits light having a wavelength within the range of 250 to 500 nm, or, by using one which combines a high-pass filter and low-pass filter, it is possible to selectively transmit light having a wavelength within the range of 250 to 500 nm. It is preferable to use a band-pass filter in terms of ease.

Moreover, when light irradiated from a light-emitting device has a wavelength deviated from the range of 250 to 500 nm, it is preferable to combine this light-emitting device with the band-pass filter for use.

As the aforementioned low-pass filter, for example, one which transmits light having a wavelength of 500 nm or less is used. As the aforementioned high-pass filter, for example, one which transmits light having a wavelength of 250 nm or more is used.

The range of the wavelength of light irradiated onto an object in the oral cavity is more preferably 330 nm to 470 nm, even more preferably 380 to 420 nm and particularly preferably 395 to 410 nm.

As the aforementioned light source, a light-emitting diode is more preferable in terms of portability and simplicity. Additionally, considering safety to the eyes, skin, or the like, practically, light irradiated onto the object is, more preferably, visible light.

FIG. 1 shows one example of an embodiment of the dental-plaque detection system which is favorably used for performing the dental-plaque detection method of the present invention.

The dental-plaque detection system of the present embodiment is roughly constituted from the following: the dental-plaque staining agent of the present invention having the aforementioned constitution, a light-emitting apparatus 10 which outputs light having a wavelength within a range of 250 to 500 nm to an object 40 in the oral cavity which is attached with the dental-plaque staining agent, an image-displaying apparatus 20 such as a personal computer and a probe (handpiece) 30, each of which is connected to the light-emitting apparatus 10, and a high-pass filter 45, which is placed forward of the probe 30 (the object side).

The light-emitting apparatus 10 has a light-emitting section 16 and light-receiving section 17, and a light source 12 and band-pass filter 15, which selectively transmits light having a wavelength within the range of 250 to 500 nm, are provided in the light-emitting section 16.

As the light source 12, a light-emitting device such as the aforementioned light-emitting diode (LED) or a lamp such as the aforementioned xenon lamp is used.

The band-pass filter 15 is one which selectively transmits light having a wavelength within the range of preferably 250 to 500 nm and more preferably 330 nm to 410 nm.

In this light-emitting section 16, among the light outputted from the light source 12, only light L, which has a wavelength within the range of 250 to 500 nm, more preferably of 330 to 410 nm, is transmitted by the band-pass filter 15.

Note that when the light-emitting device provided in the light source 12 is one which only irradiates light having a wavelength within the range of 250 to 500 nm, the band-pass filter 15 may not be provided in the light-emitting apparatus 10.

The probe 30 is connected to the light-emitting section 16 of the light-emitting apparatus 10 via a first cable 35, which has an optical waveguide such as an optical fiber. Moreover, the probe 30 is connected to the light-receiving section 17 of the light-emitting apparatus 10 via a second cable 36, which has an optical waveguide such as an optical fiber.

The first cable 35 is capable of guiding the light L outputted from the light-emitting section 16 of the light-emitting apparatus 10 and propagating it to the probe 30. The probe 30 is capable of irradiating the light L, which is propagated from the first cable 35 towards the object 40. In addition, this probe 30 is capable of sending image information of the object 40 on which the light L is irradiated, to the light-receiving section 17 of the light-emitting apparatus 10 via the second cable 36.

The high-pass filter 45 is configured so that among the reflection R of the light L, which is irradiated onto the object 40 from the probe 30, the reflection having a wavelength of 520 nm or more is transmitted. The reflection R which transmitted the high-pass filter 45 is included in the image information sent to the light-receiving section 17.

When dental-plaques are present on the object 40, the dental-plaque staining agent which is attached to dental plaques is excited by the light L and emits fluorescence, and the reflection R which transmitted the high-pass filter 45 is sent to the light-receiving section 17.

The image displaying apparatus 20 is configured so that it is capable of displaying image information of the object 40 which is received at the light-receiving section 17 of the light-emitting apparatus 10.

In order to detect dental plaques using the dental-plaque detection system of the present embodiment, the dental-plaque staining agent of the present invention of the aforementioned constitution is attached to the object 40 in the oral cavity by the method described earlier and thereafter, the probe 30 is brought close to the object 40 and while monitoring the object 40 by the image displaying apparatus 20, the light L, which has a wavelength within the range of 250 to 500 nm, is outputted from the light-emitting section 16 of the light-emitting apparatus 10 to irradiate onto the object 40. For example, when the light source 12 is a lamp, which outputs light having a long wavelength (white light), and the band-pass filter 15 is one which selectively transmits light having a wavelength of 290 to 450 nm, the light L outputted from the light-emitting section 16 will be blue- to violet-tinged light. When dental plaques are present on the object 40, only dental plaques are stained with fluorescent colors (for example, fluorescent colors other than bluish color or yellow-tinged fluorescent color). Since the sites other than dental plaques (such as parts of the surface of teeth where dental plaques are absent, interdental parts and gums) are not stained, the object 40 seen on the image displaying apparatus 20 appears with shining dental plaques and thus, dental plaques can easily be visually identified. As described so far, the dental-plaque detection system of the present embodiment is excellent in the detection accuracy of dental plaques, and in particular dental plaques at the initial phase of their formation can also be detected with good accuracy. Moreover, since the dental-plaque sites are not visually recognized under natural light, discomfort problems due to staining can be improved.

When the high-pass filter 45 is provided, since reflection other than fluorescence is not transmitted (i.e. light having a short wavelength of less than 520 nm is filtered out), only the reflection having a wavelength of 520 nm or more can be received by the light-receiving section 17 and noise light is eliminated. Thereby, the object projected on the image displaying apparatus 20 appears with only the parts where dental plaques are present shining, and thus the detection sensitivity of dental plaques can be enhanced.

Figure 2:
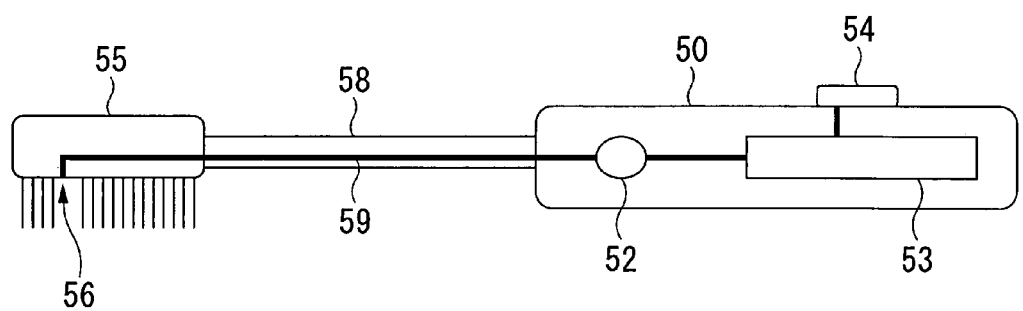
FIG. 2 is a schematic configuration diagram showing one example of an embodiment of the toothbrush attached with a light source for dental-plaque detection of the present invention.

FIG. 2 shows one example of an embodiment of the toothbrush attached with a light source for dental-plaque detection which is favorably used for performing the dental-plaque detection method of the present invention.

The toothbrush attached with a light source for dental-plaque detection shown in FIG. 2 has a grip section 50, head section 55 where a brush is arranged, and a hand grip section 58, which connects the grip section 50 and head section 55. Inside the grip section 50, a light source 52 having a light-emitting device, which outputs light having a wavelength within the range of 250 to 500 nm, and a battery box 53 where batteries, which supply electric power to the light source 52, are housed are provided. Outside the grip section 50, a switch 54, which turns the power supply to the light source 52 on and off, is provided. On the brush side of the head section 55, a light-emitting orifice 56 which outputs light, which is outputted from the light-emitting device, to an object in the oral cavity, which is attached with the dental-plaque staining agent of the present invention, is formed. An optical waveguide 59, which is composed from an optical fiber or the like, is formed between the light-emitting orifice 56 and light source 52.

In the toothbrush attached with a light source for dental-plaque detection with such a configuration, light having a wavelength within a range of 250 to 500 nm is outputted from the light-emitting device of the light source 52 by turning on the switch 54 and further, this light passes through the optical waveguide 59 and is outputted to the outside from the light-emitting orifice 56.

Figure 3:
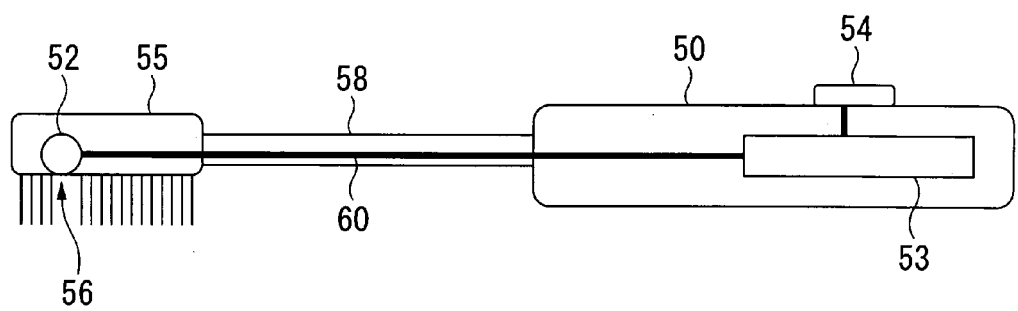
FIG. 3 is a schematic configuration diagram showing another example of the embodiment of the toothbrush attached with a light source for dental-plaque detection of the present invention.

FIG. 3 shows another example of an embodiment of the toothbrush attached with a light source for dental-plaque detection which is favorably used for performing the dental-plaque detection method of the present invention.

The toothbrush attached with a light source for dental-plaque detection shown in FIG. 3 is particularly different from the toothbrush attached with a light source for dental-plaque detection shown in FIG. 2 in that the former is provided with the light source 52 inside the head section 55, which is in the vicinity of the light-emitting orifice 56, and this light source 52 and the battery box 53 are connected by a wiring 60.

In order to detect dental plaques using the toothbrush attached with a light source for dental-plaque detection shown in FIG. 2 or 3, for example, the aforementioned dental-plaque staining agent of the present invention is attached to the object in the oral cavity by the method described earlier and thereafter, the head section 55 is brought close to the object and the switch 54 is turned on while monitoring the object by a mirror or the like, and light which has a wavelength within the range of 250 to 500 nm is irradiated onto the object.

When dental plaques are present on the object, only dental plaques are stained with fluorescent colors and since the sites other than dental plaques are not stained, the object seen on the mirror appears with shining dental plaques and thus, dental plaques can easily be visually identified. As described so far, by using the toothbrush attached with a light source for dental-plaque detection of the present invention, the detection accuracy of dental plaques can be enhanced.

Figure 4A:
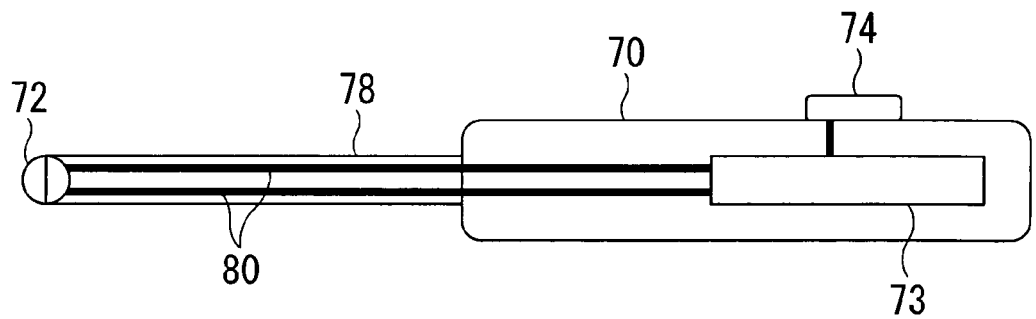
FIG. 4A is a schematic configuration diagram showing one example of an embodiment of the illuminator for dental-plaque detection of the present invention.

FIG. 4A shows one example of an embodiment of the illuminator for dental-plaque detection which is favorably used for performing the dental-plaque detection method of the present invention.

The illuminator for dental-plaque detection shown in FIG. 4A is a penlight type, which has a grip section 70 and straight stick section 78. A light source 72 having a light-emitting device, which outputs light having a wavelength within the range of 250 to 500 nm to the object in the oral cavity which is attached with the dental-plaque staining agent of the present invention, is provided in the front end of the stick section 78. Inside the grip section 70, a battery box 73 housing batteries, which supply electric power to the light source 72, is provided. Outside the grip section 70, a switch 74, which turns the power supply to the light source 72 on and off, is provided. The light source 72 and the battery box 73 are connected by a wiring 80.

In the illuminator for dental-plaque detection with such a configuration, light having a wavelength within the range of 250 to 500 nm is outputted from the light-emitting device of the light source 72 by turning on the switch 74.

Figure 4B:
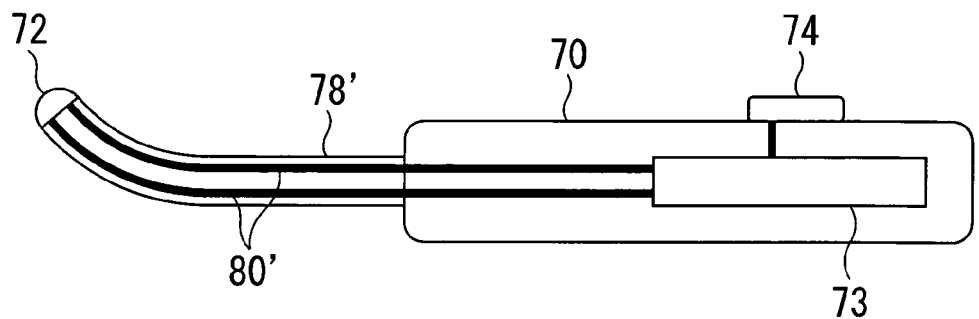
FIG. 4B is a schematic configuration diagram showing one example of another embodiment of the illuminator for dental-plaque detection of the present invention.

In addition, FIG. 4B shows another penlight-type illuminator where front ends of the stick section 78' and wiring 80 are bent. Although FIG. 4B shows an embodiment with an angle of bending of 30 degrees, usually, one with an angle of bending of approximately 10 to 50 degrees is preferable.

Figure 4C:
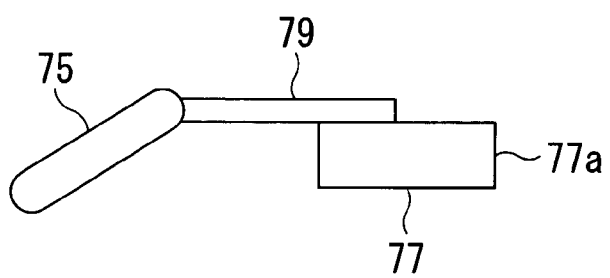
FIG. 4C is a schematic configuration diagram showing one example of an embodiment of a mirror which is either a fixed type or a removable type and is attachable to the illuminator for dental-plaque detection of the present invention.
Figure 4D:
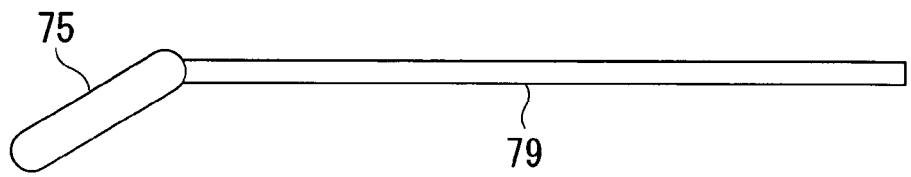
FIG. 4D is a schematic configuration diagram showing one example of an embodiment of a mirror unit which can be used concomitantly with the illuminator for dental-plaque detection of the present invention.

Furthermore, in the illuminator for dental-plaque detection of the present invention, where necessary, it is possible to attach a mirror stick section 79, mirror section 75, which is mounted onto the front end of the mirror stick section 79, and mirror, which has a cap section 77 mounted onto the back end of the mirror stick section as shown in FIG. 4C. The mirror with such a structure can be mounted by fitting the back end section 77a of the cap section 77 in, for example, the front end section of the stick section 78 (or 78') of FIG. 4A (or 4B) in a fixed manner (integrated type) or a removable manner.

Alternatively, it is also possible to use a mirror unit having the mirror stick section 79 and mirror section 75, which is mounted on the front end of the mirror stick section, concomitantly with the illuminator for dental-plaque detection of the present invention.

Figure 5:
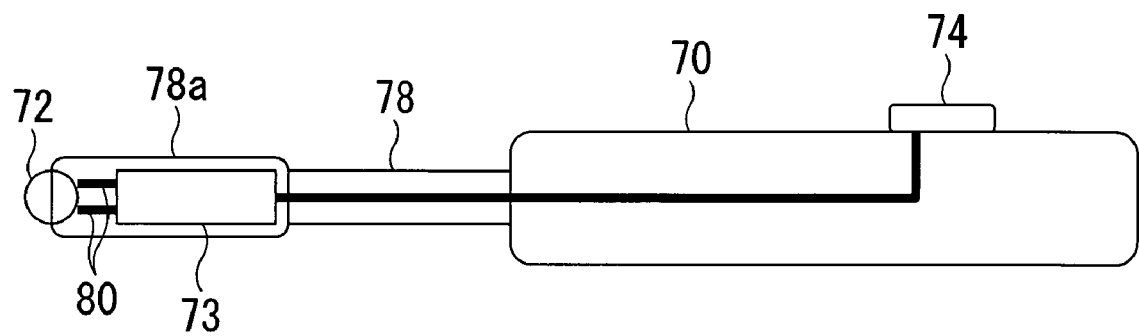
FIG. 5 is a schematic configuration diagram showing another example of the embodiment of the illuminator for dental-plaque detection of the present invention.

FIG. 5 shows another example of the embodiment of the illuminator for dental-plaque detection which is favorably used for performing the dental-plaque detection method of the present invention.

The illuminator for dental-plaque detection shown in FIG. 5 is particularly different from the illuminator for dental-plaque detection shown in FIG. 4 in that a diameter-expanding section 78a is provided at the front end part of the stick section 78, a battery box 73 is provided inside the diameter-expanding section 78a, and the light source 72, which is at the front end of the stick section 78, and battery box 73 are connected by the wiring 80.

In order to detect dental plaques using the illuminator for dental-plaque detection shown in FIG. 4 or 5, for example, the dental-plaque staining agent of the present invention with the aforementioned constitution is attached to the object in the oral cavity by the method described earlier and thereafter, the front end of the stick section 78 is brought close to the object and the switch 74 is turned on while monitoring the object by a mirror or the like, and light which has a wavelength within the range of 250 to 500 nm is irradiated onto the object.

When dental plaques are present on the object, only dental plaques are stained with fluorescent colors and since the sites other than dental plaques are not stained, the object seen on the mirror appears with shining dental plaques and thus, dental plaques can easily be visually identified. As described so far, by using the illuminator for dental-plaque detection of the present invention, the detection accuracy of dental plaques can be enhanced.

In the toothbrush attached with a light source for dental-plaque detection or the illuminator for dental-plaque detection of the aforementioned embodiments, it is also possible to use, within a range where performance and safety thereof are not impaired and where necessary, a light source composed from a plurality of light-emitting devices (for example, the light source may be provided with a plurality of light-emitting diodes of green light, red light, white light, or the like, and, for example, is configured so that white light and light having a wavelength within the range of 250 to 500 nm can freely be switched, or is configured so that the light-emitting diodes of same quality are bundled).

Although the intensity of light irradiated onto the object in the oral cavity is arbitrary, a level which does not have harmful effects on the oral mucosa, eyes, or the like is preferable.

Additionally, for improving the visibility of sites where the dental-plaque staining agent is attached, it is also possible to use a filter, which eliminates light (noise) interfering with the visibility or which has a capability to make the fluorescence emitted from the sites, to which dental-plaque staining agent is attached, clearer and the material quality, color, thickness, or the like of the filter is not particularly limited. For example, commercially available cellophanes, films, plastic lenses/plates, glass lenses/plates, or the like which are colored orange, yellow, or the like can be used. Moreover, it is possible to use a high-pass filter or the like which transmits fluorescence emitted from dental plaques and/or dental calculi due to the excitation light of a specific wavelength. Furthermore, it is also possible to use filters colored orange, yellow, or the like by pasting them on a mirror. By observing the sites where dental-plaque staining agent is attached through such filters, the visibility of dental plaques is improved.

The aforementioned dental-plaque staining agent of the present invention, which is used in the aforementioned dental-plaque detection system, can be sold alone as a dental-plaque staining agent for a dental-plaque detection system. Moreover, this dental-plaque staining agent for a dental-plaque detection system can be used as a dental-plaque staining agent, which is used when detecting dental plaques using the aforementioned toothbrush attached with a light source for dental-plaque detection or the aforementioned illuminator for dental-plaque detection.

Although the present invention is described in detail below by showing Examples, the present invention is not limited to the Examples below. Note that "%" in the Examples below refers to mass %.

EXPERIMENTAL METHOD

Each of dental-plaque staining agents having compositions shown below was prepared. In addition, various light sources or light-emitting sections, which were equipped with light sources, shown below were prepared. Dental plaques were detected by various dental-plaque detection methods (Examples 1 to 12 and Comparative Examples 1 to 15) using prepared dental-plaque staining agents and light sources or light-emitting sections, which were equipped with light sources (Tables 1 to 2).

A plurality of subjects (A to E) did not brush their teeth for 24 hours before using each respective dental-plaque staining agent so that the amount of dental-plaque accumulation did not affect the extent of the attached amount of staining agents (dental plaques at the initial phase of their formation). Thereafter, a dental-plaque staining agent was coated onto tooth surfaces, gums, and interdental parts with a swab and after a brief mouthwash, light was emitted from the light source or the light-emitting section to observe visibility of dental plaques and staining amount of gums and interdental parts. Furthermore, the visibility of dental plaques was observed through a filter. Observations were made under natural light in examples where the light source or the light-emitting section was not used. Observed results are shown in Table 3.

Example 1

| TS Yellow M (*1) | 50% |
|---|---|
| Water | the rest |

(*1) Yellow pigment of beni-koji manufactured by Taisho Technos Co., Ltd. (color valence 63.1)

Example 2

| TS Yellow M(*2) | 30% |
|---|---|
| Sodium lauryl sulfate | 0.5% |
| Sodium saccharin | 0.1% |
| Ethanol | 3.0% |
| Xylitol | 1.0% |
| Polyoxyethylene (60) hardened castor oil | 0.5% |
| Sodium carboxymethylcellulose | 0.5% |

-continued

| | |
|---|---|
| Propylene glycol | 2.0% |
| Perfume | 0.5% |
| Water | the rest |

(*2) Yellow pigment of beni-koji manufactured by Taisho Technos Co., Ltd. (color valence 65.5)

Example 3

Concomitant Use of a Filter in Example 2
Filter: Yellow Filter Y52 polished (manufactured by Inspektor Research Systems)

Example 4

Combination of the Dental-Plaque Staining Agent of Example 2 and the Light Source Below
Light source: VL-6LC (manufactured by Vilber Lourmat)
Light wavelength: 254 nm

Example 5

Combination of the Dental-Plaque Staining Agent of Example 2 and the Light Source Below
Light source: Lamp type light-emitting diode SDL-10N3HB (manufactured by Sander Electronic Co., Ltd.)
Light wavelength: 470 nm

Example 6

| | |
|---|---|
| TS Yellow MP (*3) | 5.0% |
| Sodium saccharin | 0.8% |
| Glycerin | 10.0% |
| Xylitol | 0.5% |
| Polyoxyethylene (100) hardened castor oil | 0.3% |
| Perfume | 0.2% |
| Water | the rest |

(*3) Yellow pigment of beni-koji manufactured by Taisho Technos Co., Ltd. (color valence 120.0)

Example 7

Concomitant Use of a Filter in Example 6
Filter: Yellow No. 8 (manufactured by Kenko Co., Ltd.)

Example 8

| | |
|---|---|
| TS Yellow MP (*4) | 20% |
| Sodium lauryl sulfate | 0.5% |
| Sodium saccharin | 0.1% |
| Ethanol | 3.0% |
| Water | the rest |

(*4) Yellow pigment of beni-koji manufactured by Taisho Technos Co., Ltd. (color valence 123.2)

Example 9

| | |
|---|---|
| Curcumin AL (*5) | 10% (equivalent to 0.92% as turmeric pigment) |
| Propylene glycol | 6.0% |

-continued

| | |
|---|---|
| Sodium lauryl sulfate | 1.0% |
| Sodium saccharin | 0.25% |
| Water | the rest |

(*5) manufactured by San-Ei Gen F.F.I., Inc. (9.2% included as turmeric pigment)

Example 10

Concomitant Use of a Filter in Example 9
Filter: Yellow Filter Y52 polished (manufactured by Inspektor Research Systems)

Example 11

| | |
|---|---|
| Curcumin (*6) | 0.5% |
| Sodium lauryl sulfate | 0.5% |
| Sodium saccharin | 0.3% |
| Ethanol | 4.0% |
| Phloxine B (Red No. 104 *7) | 0.01% |
| Water | the rest |

(*6) manufactured by Wako Pure Chemical Industries, Ltd.
*7) manufactured by Wako Pure Chemical Industries, Ltd.

Example 12

Concomitant Use of a Filter in Example 11
Filter: Use of a yellow cellophane paper by being pasted onto a mirror (manufactured by LT Co., Ltd.)

Comparative Example 1

Use of the Dental-Plaque Staining Agent of Example 2 Alone

Comparative Example 2

Combination of the Dental-Plaque Staining Agent of Example 2 and the Light Source Below
Light source: Lamp type light-emitting diode SDL-10N3SPG (manufactured by Sander Electronic Co., Ltd.)
Light wavelength: 525 nm

Comparative Example 3

Combination of the Dental-Plaque Staining Agent of Example 2 and the Light Source Below
Light source: Lamp type light-emitting diode SDL-5N3TY (manufactured by Sander Electronic Co., Ltd.)
Light wavelength: 590 nm

Comparative Example 4

Combination of the Dental-Plaque Staining Agent of Example 2 and the Light Source Below
Light source: Lamp type light-emitting diode SDL-10N3TR (manufactured by Sander Electronic Co., Ltd.)
Light wavelength: 630 nm

Comparative Example 5

Use of the Dental-Plaque Staining Agent of Example 6 Alone

Comparative Example 6

Use of the Dental-Plaque Staining Agent of Example 9 Alone

Comparative Example 7

Use of the Dental-Plaque Staining Agent of Example 11 Alone

Comparative Example 8

| | |
|---|---|
| Erythrosine B (Red No. 3 pigment *8) | 3.0% |
| Sodium lauryl sulfate | 0.5% |
| Sodium saccharin | 0.1% |
| Water | the rest |

*8) manufactured by Wako Pure Chemical Industries, Ltd.

Comparative Example 9

| | |
|---|---|
| Dental Plaque Disclosing Solution (*9) (sodium fluorescein 0.75%) | |
| Light-emitting section: PLAK-LITE Illuminator (*10) | |

(*9) manufactured by CrossField Co., Ltd.
(*10) manufactured by CrossField Co., Ltd.

Comparative Example 10

| | |
|---|---|
| Blue pigment from Spirulina (*11) | 1.0% |
| Sodium lauryl sulfate | 0.5% |
| Sodium saccharin | 0.1% |
| Water | the rest |

(*11) manufactured by Kanto Chemical Co., Inc. (fluorochrome)

Light source: Lamp type light-emitting diode L405-06V (manufactured by Epitex Inc.)
Light wavelength: 405 nm

Comparative Example 11

| | |
|---|---|
| Sodium copperchlorophyllin (*12) | 1.0% |
| Sodium lauryl sulfate | 0.5% |
| Sodium saccharin | 0.1% |
| Water | the rest |

(*12) manufactured by Wako Pure Chemical Industries, Ltd. (aqueous pigment where central element of magnesium in chlorophyll is replaced with copper)

Light source: Lamp type light-emitting diode L405-06V (manufactured by Epitex Inc.)
Light wavelength: 405 nm

Comparative Example 12

Use of the Light Source Below Alone
Light source: VL-6LC (manufactured by Vilber Lourmat)
Light wavelength: 254 nm

Comparative Example 13

Use of the Light Source Below Alone
Light source: Lamp type light-emitting diode L405-06V (manufactured by Epitex Inc.)
Light wavelength: 405 nm

Comparative Example 14

Use of the Light Source Below Alone
Light source: Lamp type light-emitting diode SDL-10N3HB (manufactured by Sander Electronic Co., Ltd.)
Light wavelength: 470 nm

Comparative Example 15

Use of the Light Source Below Alone
Light source: Lamp type light-emitting diode SDL-5N3TY (manufactured by Sander Electronic Co., Ltd.)
Light wavelength: 590 nm

TABLE 1

| Ex. | Staining agent | Conc. % | Light source | Wavelength nm | Filter |
|---|---|---|---|---|---|
| 1 | Beni-koji yellow (liquid) | 1 | Lamp type | 405 | — |
| 2 | Beni-koji yellow (liquid) | 0.5 | QLF | 370 ± 40 | — |
| 3 | Beni-koji yellow (liquid) | 0.5 | QLF | 370 ± 40 | High-pass |
| 4 | Beni-koji yellow (liquid) | 0.5 | UV lamp | 254 | — |
| 5 | Beni-koji yellow (liquid) | 0.5 | Lamp type | 470 | — |
| 6 | Beni-koji yellow (powder) | 0.1 | Lamp type | 405 | — |
| 7 | Beni-koji yellow (powder) | 0.1 | Lamp type | 405 | Yellow filter |
| 8 | Beni-koji yellow (powder) | 0.03 | QLF | 370 ± 40 | High-pass |
| 9 | Turmeric pigment | 0.92 | QLF | 370 ± 40 | — |
| 10 | Turmeric pigment | 0.92 | QLF | 370 ± 40 | High-pass |
| 11 | Curcumin + Red 104 | 0.5 | Lamp type | 405 | — |
| 12 | Curcumin + Red 104 | 0.5 | Lamp type | 405 | Yellow cellophane |

TABLE 2

| Comp. Ex. | Staining agent | Conc. % | Light source | Wavelength nm | Filter |
|---|---|---|---|---|---|
| 1 | Beni-koji yellow (liquid) | 0.5 | — | — | — |
| 2 | Beni-koji yellow (liquid) | 0.5 | Lamp type | 525 | — |
| 3 | Beni-koji yellow (liquid) | 0.5 | Lamp type | 590 | — |
| 4 | Beni-koji yellow (liquid) | 0.5 | Lamp type | 630 | — |
| 5 | Beni-koji yellow (powder) | 0.1 | — | — | — |
| 6 | Turmeric pigment | 0.92 | — | — | — |
| 7 | Curcumin + Red 104 | 0.5 | — | — | — |
| 8 | Red No. 3 | 3 | — | — | — |
| 9 | Fluorescein | 0.75 | Plaklite | Not determined | — |
| 10 | Spirulina blue pigment | 1 | Lamp type | 405 | — |
| 11 | Sodium copperchlorophyllin | 1 | Lamp type | 405 | — |
| 12 | — | — | UVlamp | 254 | — |
| 13 | — | — | Lamp type | 405 | — |
| 14 | — | — | Lamp type | 470 | — |
| 15 | — | — | Lamp type | 590 | — |

TABLE 3

| Observed site | Subject A D.P. | Subject A Gum | Subject A Inter. | Subject B D.P. | Subject B Gum | Subject B Inter. | Subject C D.P. | Subject C Gum | Subject C Inter. | Subject D D.P. | Subject D Gum | Subject D Inter. | Subject E D.P. | Subject E Gum | Subject E Inter. |
|---|---|---|---|---|---|---|---|---|---|---|---|---|---|---|---|
| Ex. 1 | 5 | 5 | 5 | 5 | 5 | 5 | 5 | 5 | 5 | — | — | — | — | — | — |
| Ex. 2 | 5 | 5 | 5 | 5 | 5 | 5 | 5 | 5 | 5 | 5 | 5 | 5 | 5 | 5 | 5 |
| Ex. 3 | 5 | 5 | 5 | 5 | 5 | 5 | 5 | 5 | 5 | 5 | 5 | 5 | 5 | 5 | 5 |
| Ex. 4 | 5 | 5 | 5 | 4 | 5 | 5 | 4 | 5 | 5 | — | — | — | — | — | — |
| Ex. 5 | 4 | 5 | 5 | 5 | 5 | 5 | 4 | 5 | 5 | 5 | 5 | 5 | — | — | — |
| Ex. 6 | 4 | 5 | 5 | 5 | 5 | 5 | 4 | 5 | 5 | 4 | 5 | 5 | — | — | — |
| Ex. 7 | 5 | 5 | 5 | 5 | 5 | 5 | 5 | 5 | 5 | 5 | 5 | 5 | — | — | — |
| Ex. 8 | 3 | 5 | 5 | 3 | 5 | 5 | 3 | 5 | 5 | — | — | — | — | — | — |
| Ex. 9 | 3 | 3 | 5 | 4 | 3 | 5 | 3 | 4 | 5 | — | — | — | 3 | 3 | 5 |
| Ex. 10 | 4 | 3 | 5 | 4 | 3 | 5 | 4 | 3 | 4 | — | — | — | 4 | 3 | 4 |
| Ex. 11 | 3 | 3 | 5 | 4 | 3 | 5 | 3 | 3 | 5 | — | — | — | — | — | — |
| Ex. 12 | 4 | 3 | 4 | 4 | 3 | 5 | 4 | 3 | 4 | — | — | — | — | — | — |
| Comp. Ex. 1 | 1 | 5 | 5 | 1 | 5 | 5 | 1 | 5 | 5 | — | — | — | — | — | — |
| Comp. Ex. 2 | 1 | 5 | 5 | 1 | 5 | 5 | 1 | 5 | 5 | — | — | — | — | — | — |
| Comp. Ex. 3 | 1 | 5 | 5 | 1 | 5 | 5 | 1 | 5 | 5 | — | — | — | — | — | — |
| Comp. Ex. 4 | 1 | 5 | 5 | 1 | 5 | 5 | 1 | 5 | 5 | — | — | — | — | — | — |
| Comp. Ex. 5 | 1 | 5 | 5 | 1 | 5 | 5 | 1 | 5 | 5 | 1 | 5 | 5 | — | — | — |
| Comp. Ex. 6 | 1 | 4 | 5 | 1 | 5 | 5 | 1 | 4 | 5 | — | — | — | 1 | 5 | 5 |
| Comp. Ex. 7 | 2 | 3 | 5 | 1 | 5 | 5 | 1 | 4 | 5 | — | — | — | — | — | — |
| Comp. Ex. 8 | 4 | 1 | 1 | 5 | 1 | 1 | 4 | 1 | 1 | 4 | 1 | 1 | 4 | 1 | 1 |
| Comp. Ex. 9 | 2 | 2 | 2 | 3 | 2 | 1 | 2 | 3 | 2 | 3 | 2 | 1 | — | — | — |
| Comp. Ex. 10 | 1 | 5 | 5 | 1 | 5 | 5 | 1 | 5 | 5 | — | — | — | — | — | — |
| Comp. Ex. 11 | 1 | 5 | 5 | 1 | 5 | 5 | 1 | 5 | 5 | — | — | — | — | — | — |
| Comp. Ex. 12 | 1 | 5 | 5 | 1 | 5 | 5 | 1 | 5 | 5 | — | — | — | — | — | — |
| Comp. Ex. 13 | 1 | 5 | 5 | 1 | 5 | 5 | 1 | 5 | 5 | 1 | 5 | 5 | 1 | 5 | 5 |
| Comp. Ex. 14 | 1 | 5 | 5 | 1 | 5 | 5 | 1 | 5 | 5 | — | — | — | — | — | — |
| Comp. Ex. 15 | 1 | 5 | 5 | 1 | 5 | 5 | 1 | 5 | 5 | 1 | 5 | 5 | 1 | 5 | 5 |

D.P: dental plaque
Inter: interdental

Evaluation of dental plaques in Table 3 was carried out in accordance with the criteria below.
5: Extremely good visibility
4: Considerably good visibility
3: Good visibility
2: Visible
1: Not visible
-: Not performed Evaluations of gum and interdental parts in Table 3 were carried out in accordance with the criteria below.
5: No amount of staining at all
4: Almost no amount of staining at all
3: A small amount of staining
2: Somewhat large amount of staining
1: A large amount of staining
-: Not performed It is seen from the results shown in Table 3 that visibility of dental plaques is remarkably improved when using the dental-plaque detection method where the dental-plaque staining agent, which contains at least one selected from the yellow pigment of beni-koji, turmeric extracts, and curcumin, is coated onto tooth surfaces, gums, and interdental parts and after a mouthwash, irradiating light having a wavelength within the range of 250 to 500 nm compared to the case where such light is not used. Moreover, it was confirmed that the aforementioned dental-plaque staining agent selectively stained dental plaques compared to the cases where the Red No. 3 pigment (which is widely used as a pigment for dental-plaque staining agents) alone was used or other pigment and light were concomitantly used. Furthermore, in the aforementioned method, it was verified that visibility of dental plaques was improved by observing the sites where the staining agent was attached through a filter.

INDUSTRIAL APPLICABILITY

According to the dental-plaque detection method of the present invention, detection accuracy of dental plaques will be excellent and moreover, the situation where sites other than dental plaques (such as interdental parts and gums) are stained can be improved.

The dental-plaque detection system, the illuminator for dental-plaque detection, the toothbrush attached with a light source for dental-plaque detection, and the dental-plaque staining agent for the dental-plaque detection system of the present invention can favorably be used in conducting the dental-plaque detection method of the present invention and they are excellent in terms of the detection accuracy of dental plaques and moreover, they can improve the situation where sites other than dental plaques (such as interdental parts and gums) are stained.

The invention claimed is:

1. A dental-plaque detection system comprising:
   a dental-plaque staining agent, which contains a yellow pigment of beni-koji having xanthomonasins as a major component; and
   a light-emitting apparatus, which outputs light having a wavelength within a range of 250 to 500 nm to an object in an oral cavity where the dental-plaque staining agent is attached.

2. The dental-plaque detection system according to claim 1, further comprising a light-emitting diode in the light-emitting apparatus which outputs light having a wavelength within a range of 250 to 500 nm.

3. The dental-plaque detection system according to claim 1, further comprising both
   a light-emitting diode or a lamp; and
   a filter, which selectively transmits light having a wavelength within a range of 250 to 500 nm, in the light-emitting apparatus.

4. The dental-plaque detection system according to claim 1, further comprising
   a light-receiving section in the light-emitting apparatus; and
   an image-displaying apparatus and a probe, each of which is connected to the light-emitting apparatus;
   wherein the probe is configured so that the light outputted from the light-emitting apparatus can be irradiated towards the object and also, image information of the object, which is irradiated with the light can be sent to the light-receiving section; and
   wherein the image displaying apparatus is configured so that the image information of the object received by the light-receiving section can be displayed.

5. The dental-plaque detection system according to claim 4, further comprising a high-pass filter which transmits light having a wavelength of 520 nm or more among reflection of the light, which is irradiated onto the object.

* * * * *